United States Patent
Dehestani et al.

(10) Patent No.: US 11,583,785 B2
(45) Date of Patent: Feb. 21, 2023

(54) SYSTEMS AND METHODS FOR CANNABIS EXTRACTION

(71) Applicant: Cannacraft, Inc., Santa Rosa, CA (US)

(72) Inventors: Ahmad Dehestani, Walnut Creek, CA (US); Farhad Fazlollahi, Rohnert Park, CA (US); Dennis F. Hunter, Rohnert Park, CA (US)

(73) Assignee: Cannacraft, Inc., Santa Rosa, CA (US)

( * ) Notice: Subject to any disclaimer, the term of this patent is extended or adjusted under 35 U.S.C. 154(b) by 0 days.

(21) Appl. No.: 17/075,767

(22) Filed: Oct. 21, 2020

(65) Prior Publication Data

US 2021/0354047 A1    Nov. 18, 2021

Related U.S. Application Data

(60) Provisional application No. 63/024,839, filed on May 14, 2020.

(51) Int. Cl.
| | | |
|---|---|---|
| *B01D 11/02* | (2006.01) | |
| *A61K 36/18* | (2006.01) | |
| *A61K 36/185* | (2006.01) | |

(52) U.S. Cl.
CPC ........ *B01D 11/0203* (2013.01); *A61K 36/185* (2013.01); *B01D 11/0284* (2013.01); *B01D 11/0288* (2013.01); *B01D 11/0292* (2013.01)

(58) Field of Classification Search
CPC ... B01D 1/00; B01D 1/26; B01D 3/10; B01D 11/02; B01D 11/0203; B01D 11/0211; B01D 11/028; B01D 11/0284; B01D 11/0288; B01D 11/0292; B01D 11/0403; B01D 15/08; B01D 17/00; B01D 17/005; B01D 39/06; B01D 2011/007; A61K 36/00; A61K 36/16; A61K 36/185; A61K 36/268; A61K 36/53; A61K 36/532; A61K 36/62; A61K 36/896; A61K 36/906; A61K 36/9066; A61L 2/005; A61L 2/0011; A61L 2/0017; A61L 2/0047; A61L 2/0064; A61L 2/02; A61L 2/022; A61L 2/10; A61L 2/12; A61L 2/202; A61L 2202/21;
(Continued)

(56) References Cited

U.S. PATENT DOCUMENTS

| | | | | |
|---|---|---|---|---|
| 4,877,530 A | * | 10/1989 | Moses | ................ B01D 11/0407 210/511 |
| 11,000,818 B1 | * | 5/2021 | Sanchez | ................... B01J 3/062 |

(Continued)

FOREIGN PATENT DOCUMENTS

CA        2455129 C   * 10/2014   ........... A61K 31/352

*Primary Examiner* — Joseph W Drodge
(74) *Attorney, Agent, or Firm* — Innovation Law LLP

(57) ABSTRACT

This disclosure provides methods and systems for the supercritical fluid extraction of cannabinoids from cannabis. The supercritical fluid extraction of cannabinoids is performed with carbon dioxide ($CO_2$) balanced with one or more hydrocarbons, such as propane, propene, and propadiene. As demonstrated, the extraction can be carried out at maximum efficiency and energy savings while keeping the wax formation at minimum by lowering temperature. The methods and systems disclosed herein reduce the production time and safety/environmental hazards and are suitable for proper and safe extraction in non-GMP and GMP environments.

13 Claims, 6 Drawing Sheets

(58) Field of Classification Search
CPC ....... C07C 37/004; C07C 39/23; C07C 45/78; C07C 45/79; C07C 45/81; C07C 45/82; C07C 45/85; C07C 49/248; C07C 49/255
See application file for complete search history.

(56) References Cited

U.S. PATENT DOCUMENTS

| | | |
|---|---|---|
| 2015/0297654 A1* | 10/2015 | Speier ................. A61K 9/7023 424/725 |
| 2017/0008870 A1* | 1/2017 | Dibble ................. C07D 311/80 |
| 2018/0056211 A1* | 3/2018 | Seabrook ................. B04C 3/06 |
| 2018/0147247 A1* | 5/2018 | Ivanov ................... A61P 27/06 |
| 2019/0153484 A1* | 5/2019 | Bray ......................... C12P 7/22 |
| 2019/0240593 A1* | 8/2019 | Murphy ................. B01D 17/12 |
| 2020/0054962 A1* | 2/2020 | Vanaman ................. B01D 3/38 |
| 2020/0215137 A1* | 7/2020 | Speier ................... A61K 36/00 |
| 2021/0236955 A1* | 8/2021 | Dehestani .......... B01D 11/0284 |
| 2021/0275618 A1* | 9/2021 | Davidson ............... A61K 36/07 |

\* cited by examiner

SYSTEMS AND METHODS FOR CANNABIS EXTRACTION

CROSS-REFERENCE TO RELATED APPLICATIONS

This application claims priority under 35 U.S.C. § 119(e) to U.S. Provisional Patent Application No. 63/024,839, filed May 14, 2020. The foregoing applications are incorporated by reference herein in its entirety.

FIELD OF THE INVENTION

This invention relates to methods and systems for supercritical fluid extraction of cannabinoids and terpenes from cannabis and more specifically relates to the supercritical fluid extraction of cannabinoids and terpenes from cannabis using carbon dioxide balanced with hydrocarbon(s).

BACKGROUND OF THE INVENTION

The chemical phenotypes of *Cannabis* are useful to classify the plant material as drug- or fiber-type varieties, based on quantitative differences in the content of main cannabinoids present. The key difference between these two is found in the potential content of the active component 9-tetrahydrocannabinol (THC). A high content of THC classifies as drug-type cannabis, while a low THC content (e.g., less than 0.2%) classifies as fiber-type cannabis or Hemp. Both THC and Cannabidiol (CBD), a non-psychoactive cannabinoid, are neutral form cannabinoids, obtained after a non-enzymatic decarboxylation process occurs to the acidic forms, 9-tetrahydrocannabinolic acid (THCA) and Cannabidiol acid (CBDA) originally present in the plant material.

Food and cosmetic products developed from natural sources are gaining global popularity because of their proven better therapeutic effects over synthetic ones. For this reason, extraction of plant-derived bioactive compounds, including functional oil, has been extensively investigated. The cold press method is the most commonly used to extract these oils, and it is deemed advantageous because of the low operating temperature suitable for keeping essential nutrients from possible thermal degradation. However, this method entails some drawbacks, including low yield.

The extraction method features essentially define the quality of the final product. The extraction of cannabis to make other forms of concentrate is a function of the solubility of THC and other cannabinoids in different organic solvents (mainly hydrocarbons and alcohols). Solvents like methanol, ethanol, chloroform, butane, hexane, etc. are currently applied. However, safety considerations related to their toxicity and flammability exist.

Accordingly, there exists a need for a method and system for cannabis extraction with improved yield and efficiency and reduced energy consumption and safety/environmental hazards.

SUMMARY OF THE INVENTION

This disclosure addresses the need mentioned above in a number of aspects. In one aspect, this disclosure provides a method for cannabis extraction. The method comprises (i) contacting cannabis plant material with a supercritical fluid solvent system comprising carbon dioxide ($CO_2$) and a hydrocarbon co-solvent; (ii) obtaining a first fraction of the supercritical fluid solvent system containing a first cannabis extract during a first period of time; (iii) obtaining a second fraction of the supercritical fluid solvent system containing a second cannabis extract during a second period of time; and (iv) removing the $CO_2$ and the hydrocarbon co-solvent from the first fraction of the supercritical fluid solvent system and the second fraction of the supercritical fluid solvent system, thereby obtaining the first cannabis extract and the second cannabis extract.

In some embodiments, the first cannabis extract comprises terpene and the second cannabis extract comprises cannabinoids. In some embodiments, the cannabis plant material comprises fresh frozen. In some embodiments, the first period of time is between about 2 minutes and about 30 minutes. In some embodiments, the second period of time is between about 30 minutes and about 24 hours.

In some embodiments, the hydrocarbon co-solvent is selected from the group consisting of propane, propene, propadiene, and a combination thereof. In some embodiments, a molar ratio of $CO_2$ to the hydrocarbon co-solvent is between about 0.75 to about 0.25 and about 0.98 to about 0.02. In some embodiments, a molar ratio of $CO_2$ to the hydrocarbon co-solvent is about 0.95 to about 0.05.

In some embodiments, the step of contacting cannabis plant material with a supercritical fluid solvent system is performed at a pressure between about 500 psi and about 800 psi. In some embodiments, the step of contacting cannabis plant material with a supercritical fluid solvent system is performed at a pressure between about 650 psi and about 800 psi. In some embodiments, the step of contacting cannabis plant material with a supercritical fluid solvent system is performed at a temperature between about 32° F. and about 38° F. In some embodiments, the step of contacting cannabis plant material with a supercritical fluid solvent system is performed at a temperature between about 34° F. and about 36° F.

In some embodiments, the cannabis extract comprises terpene oil. In some embodiments, the extraction efficiency of terpene is at least 50% higher than a predetermined reference value.

In some embodiments, the cannabis extract comprises one or more cannabinoids selected from the group consisting of: tetrahydrocannabinol (THC), cannabidiol (CBD), cannabinol (CBN), cannabigerol (CBG), cannabichromene (CBC), cannabicyclol (CBL), cannabivarin (CBV), tetrahydrocannabivarin (THCV), cannabidivarin (CBDV), cannabichromevarin (CBCV), cannabigerovarin (CBGV), cannabigerol monomethyl ether (CBGM), and a combination thereof.

In some embodiments, the cannabis plant material is processed from *Cannabis sativa* or *Cannabis indica*. In some embodiments, the method further comprises grinding *Cannabis sativa* or *Cannabis indica* into ground cannabis plant material.

In some embodiments, the wax formation during the extraction process is reduced by at least 10% compared to a predetermined reference value. In some embodiments, the wax formation during the extraction process is reduced by at least 50% compared to a predetermined reference value.

In some embodiments, the method further comprises purifying the cannabis extract by employing at least one of chromatography, adsorption, crystallization, distillation, liquid-liquid extraction, filtration, fractional distillation, precipitation, recrystallization, and sublimation.

In another aspect, this disclosure also provides a system for cannabis extraction. The system comprises (a) at least one extractor configured to receive plant material and a supercritical fluid solvent system comprising $CO_2$ and a hydrocarbon co-solvent; (b) an accumulator connected to the extractor and configured to feed the supercritical fluid solvent system to the extractor; and (c) at least one container connected to the extractor and configured to receive the extract generated from the plant material.

In some embodiments, the plant material is cannabis plant material. In some embodiments, the plant material is processed from *Cannabis sativa* or *Cannabis indica*. In some embodiments, the plant material is coffee or tea leaves.

In some embodiments, the system further comprises a first reservoir for $CO_2$ and a second reservoir for the hydrocarbon co-solvent, wherein the first reservoir and the second reservoir are connected to the accumulator and configured to feed $CO_2$ and the hydrocarbon co-solvent to the accumulator in which $CO_2$ and the hydrocarbon co-solvent are blended at a predetermined molar ratio.

In some embodiments, the system further comprises a heater connected with both the accumulator and the extractor, wherein the heater heats the supercritical fluid solvent system after the supercritical fluid solvent system passes through the plant material in the extractor, whereby the heated supercritical fluid solvent system is fed back to the accumulator.

In some embodiments, the hydrocarbon co-solvent is selected from the group consisting of propane, propene, propadiene, and a combination thereof. In some embodiments, the predetermined molar ratio of carbon dioxide to the hydrocarbon co-solvent is between about 0.75 to about 0.25 and about 0.98 to about 0.02. In some embodiments, the predetermined molar ratio of carbon dioxide to the hydrocarbon co-solvent is about 0.95 to about 0.05.

In some embodiments, the accumulator is configured to provide the supercritical fluid solvent system with a pressure between about 650 psi and about 800 psi. In some embodiments, the accumulator is configured to provide the supercritical fluid solvent system with a temperature between about 32° F. and about 38° F.

In some embodiments, the extract comprises terpene oil. In some embodiments, the extract comprises one or more cannabinoids selected from the group consisting of: tetrahydrocannabinol (THC), cannabidiol (CBD), cannabinol (CBN), cannabigerol (CBG), cannabichromene (CBC), cannabicyclol (CBL), cannabivarin (CBV), tetrahydrocannabivarin (THCV), cannabidivarin (CBDV), cannabichromevarin (CBCV), cannabigerovarin (CBGV), cannabigerol monomethyl ether (CBGM), and a combination thereof.

In some embodiments, the wax formation is reduced by at least 10% compared to a predetermined reference value.

The foregoing summary is not intended to define every aspect of the disclosure, and additional aspects are described in other sections, such as the following detailed description. The entire document is intended to be related as a unified disclosure, and it should be understood that all combinations of features described herein are contemplated, even if the combination of features are not found together in the same sentence, or paragraph, or section of this document. Other features and advantages of the invention will become apparent from the following detailed description. It should be understood, however, that the detailed description and the specific examples, while indicating specific embodiments of the disclosure, are given by way of illustration only, because various changes and modifications within the spirit and scope of the disclosure will become apparent to those skilled in the art from this detailed description.

BRIEF DESCRIPTION OF THE DRAWINGS

A clear understanding of the key features of the invention summarized above may be had by reference to the appended drawings, which illustrate the method and system of the invention, although it will be understood that such drawings depict preferred embodiments of the invention and, therefore, are not to be considered as limiting its scope with regard to other embodiments which the invention is capable of contemplating.

DETAILED DESCRIPTION OF THE INVENTION

Figure 1:
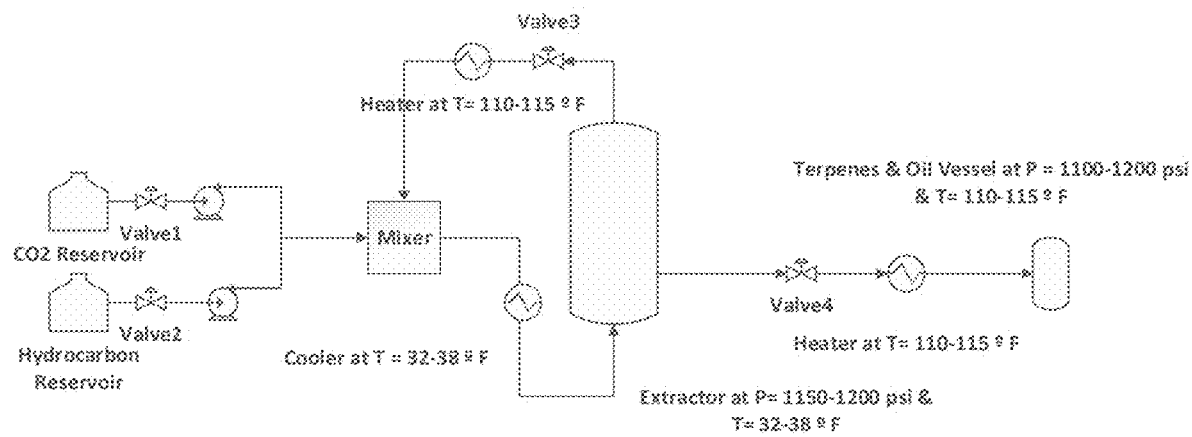
FIG. 1 is an illustration of the method and system of this invention showing a simplified end-view diagram of an extractor that has been utilized for this invention.
Figure 2:
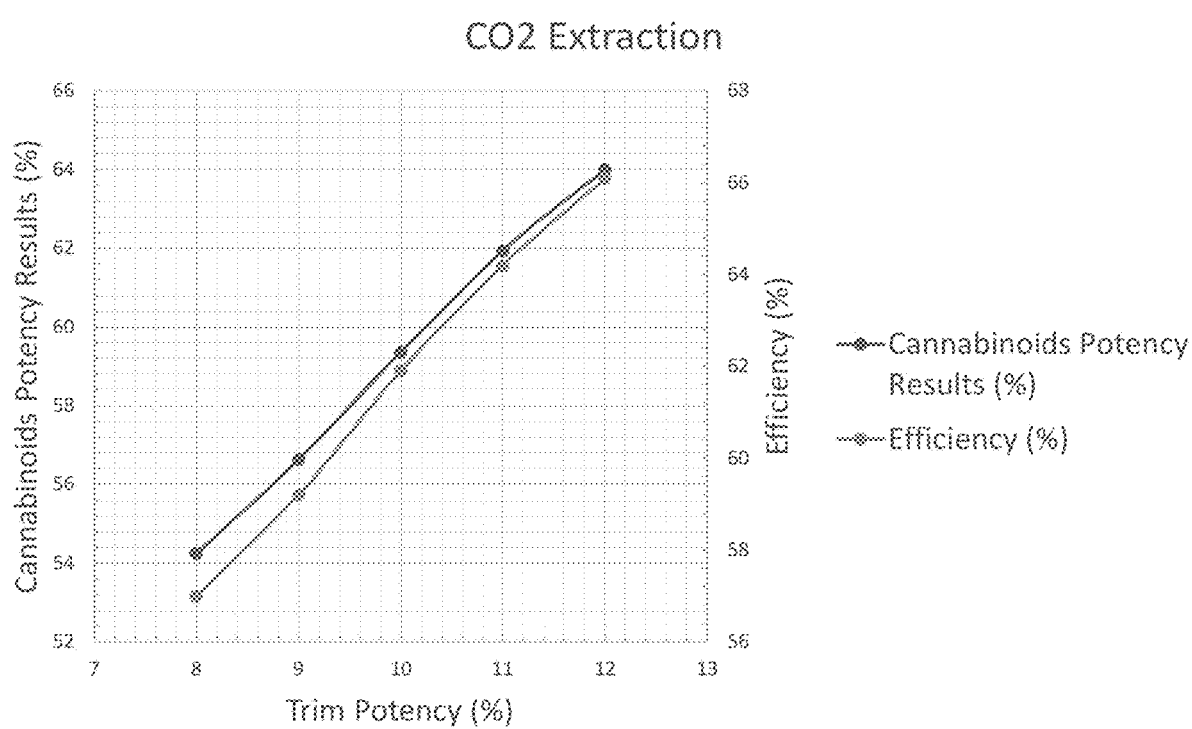
FIG. 2 is an illustration of extraction curves from $CO_2$ supercritical extraction
Figure 3:
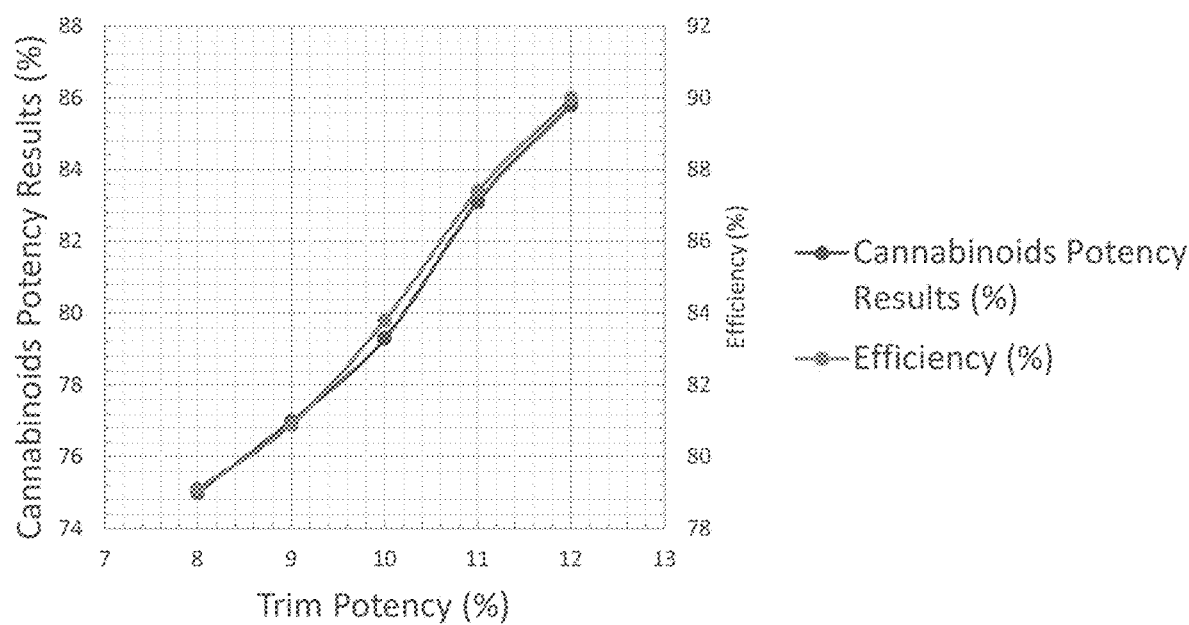
FIG. 3 is an illustration of extraction curves from 0.95 $CO_2$/0.05 propane, 0.95 $CO_2$/0.05 propene, and 0.9 $CO_2$/0.05 allene (or propadiene) extractions versus $CO_2$ only method
Figure 3:
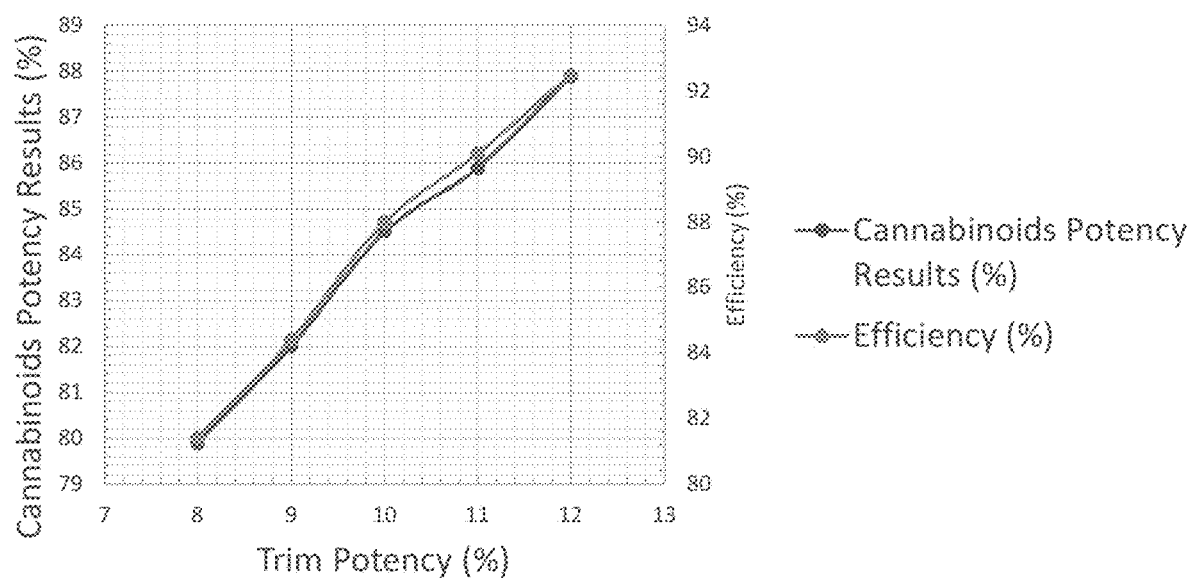
Figure 3:
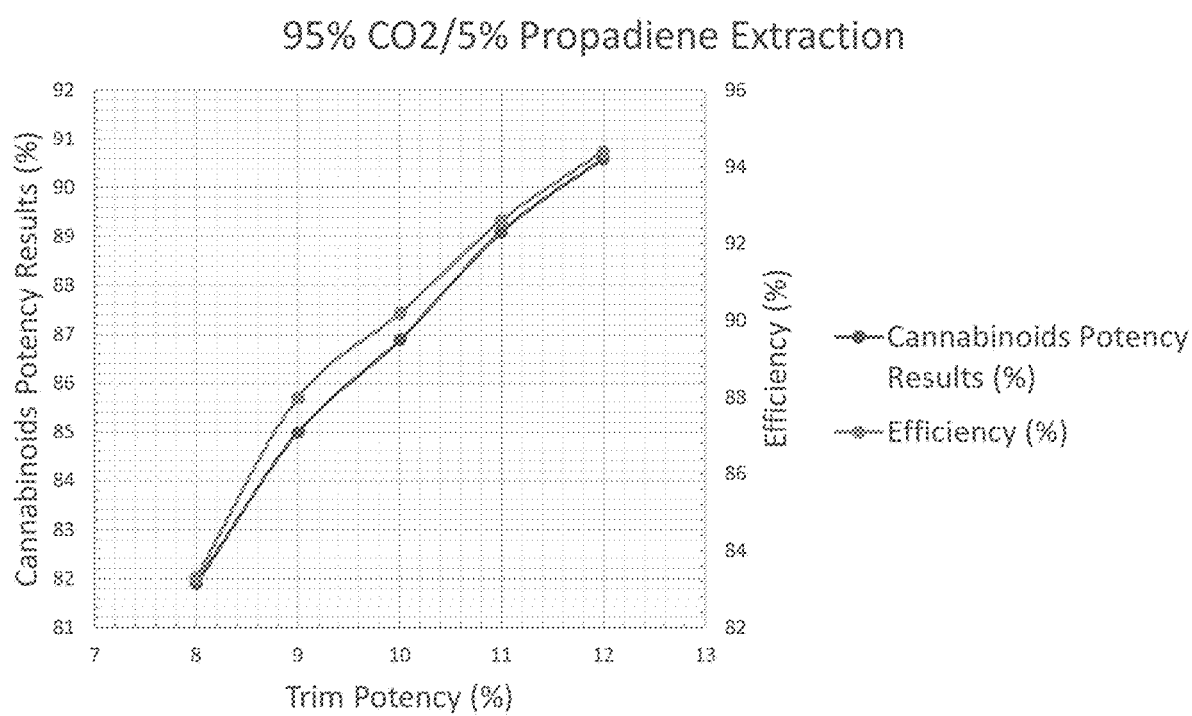
Figure 4:
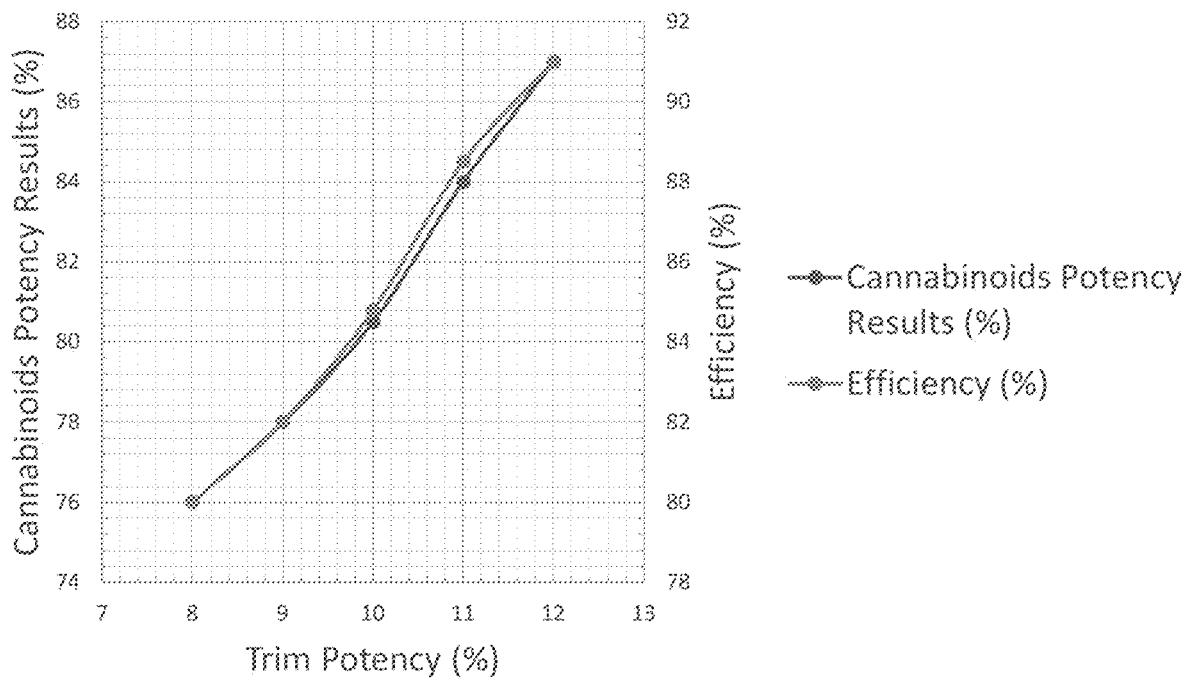
FIG. 4 is an illustration of extraction curves from 0.9 $CO_2$/0.10 propane, 0.90 $CO_2$/0.10 propene, and 0.90 $CO_2$/0.10 allene (or propadiene) extractions versus $CO_2$ only method
Figure 4:
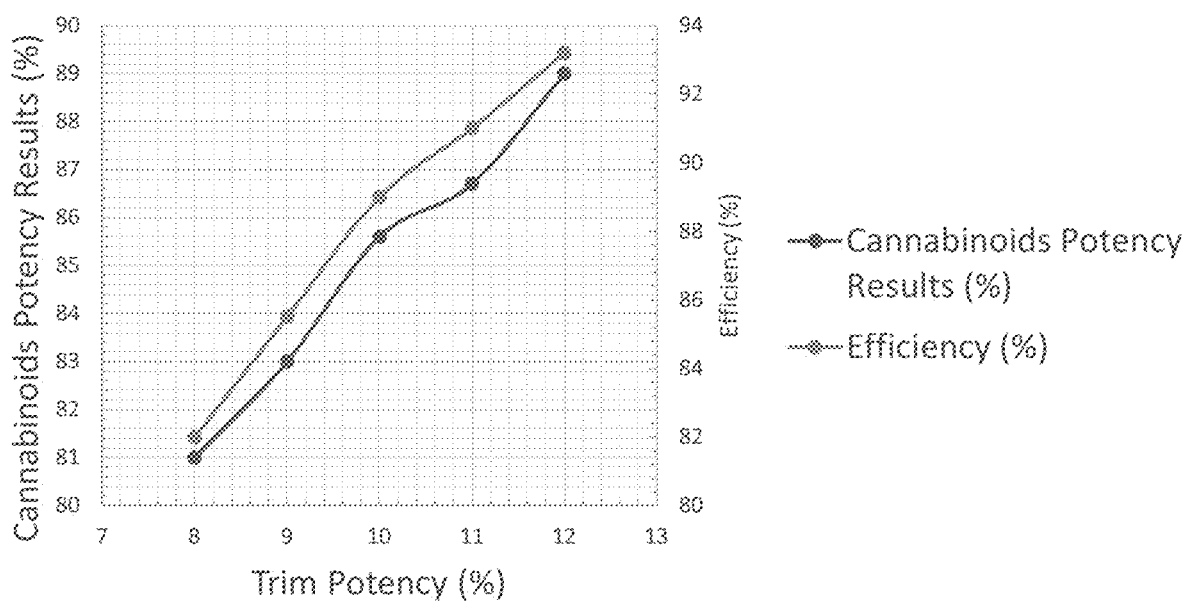
Figure 4:
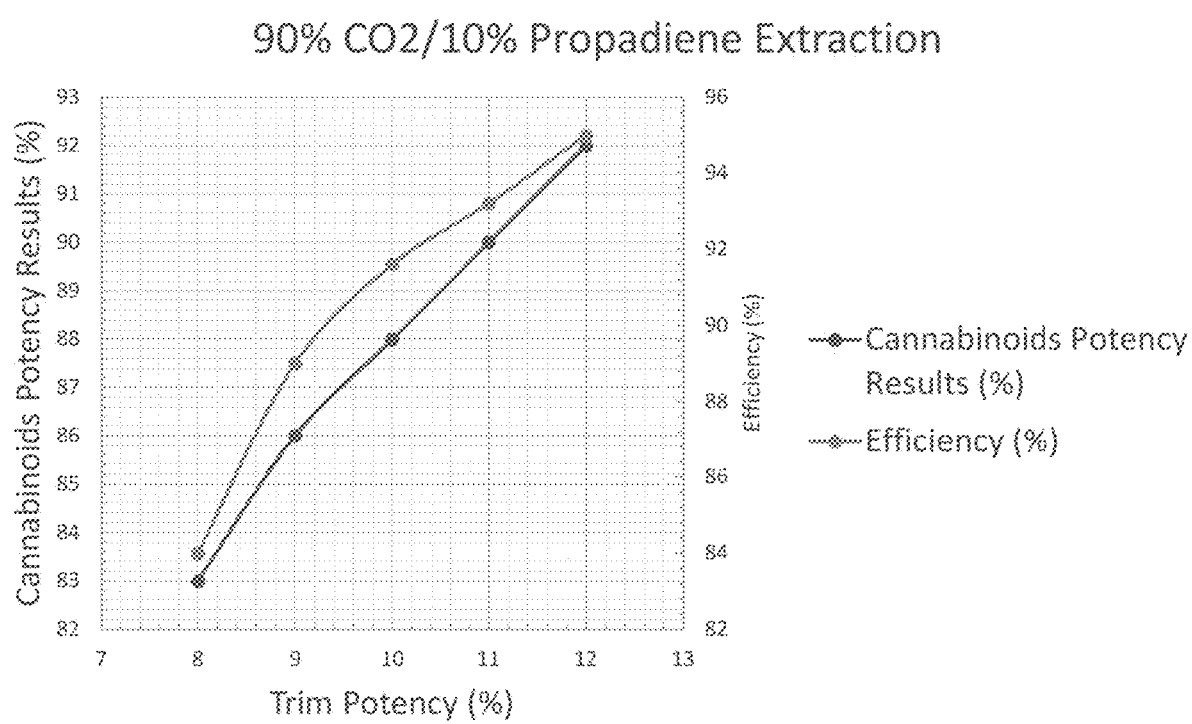

This disclosure provides methods and systems for supercritical fluid extraction of cannabinoids from cannabis. The supercritical fluid extraction of cannabinoids is performed with $CO_2$ balanced with one or more hydrocarbons, such as propane ($C_3H_8$), propene ($C_3H_6$), and propadiene ($C_3H_4$), or a combination thereof. Importantly, the extraction can be carried out at maximum efficiency and energy savings, while keeping the wax formation at a minimum by lowering temperature. The methods and systems disclosed herein reduce the production time and safety/environmental hazards and are suitable for proper and safe extraction in non-GMP and GMP environments.

A. Methods for Cannabis Extraction

In one aspect, this disclosure provides a method for cannabis extraction. The method comprises (i) contacting cannabis plant material with a supercritical fluid solvent system comprising $CO_2$ and a hydrocarbon co-solvent, to obtain a cannabis extract; and (ii) removing the supercritical fluid system from the cannabis extract. In some embodiments, steps (a) and (b) may be repeated at least once.

The method comprises (i) contacting cannabis plant material with a supercritical fluid solvent system comprising carbon dioxide ($CO_2$) and a hydrocarbon co-solvent; (ii) obtaining a first fraction of the supercritical fluid solvent system containing a first cannabis extract during a first period of time; (iii) obtaining a second fraction of the supercritical fluid solvent system containing a second cannabis extract during a second period of time; and (iv) removing the $CO_2$ and the hydrocarbon co-solvent from the first fraction of the supercritical fluid solvent system and the second fraction of the supercritical fluid solvent system, thereby obtaining the first cannabis extract and the second cannabis extract.

In some embodiments, the first cannabis extract comprises terpene and the second cannabis extract comprises cannabinoids. In some embodiments, the cannabis plant material comprises fresh frozen. In some embodiments, the first period of time is between about 2 minutes and about 30 minutes. In some embodiments, the second period of time is between about 30 minutes and about 24 hours.

"Fresh frozen," as used herein, refers to plant materials taken before they are ready for drying and trimming into buds and frozen at about −5° C. to −10° C. Fresh frozen generally contains at least 50% to 70% water by weight.

As used herein, "solvent system" refers to one or more solvents that dissolve a solute (a chemically different liquid, solid or gas), resulting in a solution. The maximum quantity of solute that can dissolve in a specific volume of solvent system varies with temperature and pressure. The solvent system can have a specified polarity and proticity. As such, solvent system can be polar, nonpolar, protic, or aprotic, wherein each of these terms is used in a relative manner.

In some embodiments, the hydrocarbon co-solvent is selected from the group consisting of propane, propene, propadiene, and a combination thereof. In some embodiments, a molar ratio of $CO_2$ to the hydrocarbon co-solvent is between about 0.75 to about 0.25 and about 0.98 to about 0.02. In some embodiments, a molar ratio of $CO_2$ to the hydrocarbon co-solvent is about 0.95 to about 0.05.

In some embodiments, the step of contacting cannabis plant material with a supercritical fluid solvent system is performed at a pressure between about 650 psi and about 800 psi. In some embodiments, the step of contacting cannabis plant material with a supercritical fluid solvent system is performed at a temperature between about 32° F. and about 38° F.

Supercritical fluids offer a variety of applications due to the properties that are easily adjusted with changing pressure and temperature. Supercritical fluids extraction (SFE) has a worldwide contribution to food, pharmaceutical, cosmetic, and oil industries as it offers very high solvent recovery, simple separation, favorable thermal conditions, mass transfer properties, solvent-free products, and healthier quality of products (M. Mukhopadhyay, et al., CRC Press, New York (2000); Fang, T., et al. Journal of Supercritical Fluids, vol. 40, no. 1: pp. 50-58 (2007)). Supercritical solvent extraction is advantageous because the solvent can be removed completely from the solutes of interest. It is an alternative method to replace or to complement conventional industrial processes, such as pressing and solvent extraction. SFE is one of the promising technologies to separate various lipids, fatty acids, essential oil, etc. due to its effluent free approach. The most frequently applied supercritical fluids include argon, methane, ethane, carbon dioxide, propane, ammonia, and water.

As used herein, $CO_2$ is used as the main fluid for extraction of cannabis products due to its superior properties. It is economical, safe, non-flammable, non-toxic (no remaining residues in extract) and reaches supercritical conditions easily (32° C. and 7.38 MPa). Also, the limitation of low polarity can be overwhelmed by the addition of a polar modifier. Furthermore, optimization of SFE process parameters is essential to achieve maximum outputs with less investment. To date, very few studies related to optimization of SFE of hemp seed oil have been reported. Carbon dioxide also has the advantage of low cost, availability, high purity, and its density is very sensitive to pressure changes around the critical region. Supercritical $CO_2$ ($scCO_2$) can dissolve low volatility substances, which enhances the concentration of solute in the supercritical phase far beyond the vapor pressure. Carbon dioxide extraction improves the efficiency, selectivity, and yield of various compounds from cannabis raw material.

SFE technique has many advantages over traditional methods, especially in preservation of thermosensitive compounds using low temperatures, which results in reduced energy consumption. The CBD and Δ9-THC that form during decarboxylation are nonpolar and soluble in supercritical $CO_2$. However, the waxes present in the flowers are also extracted by supercritical $CO_2$. The removal of these waxes through the "winterization" process can generate a desirable increase in the concentration of the cannabinoids in the extract. Syntactically, this process consists of suspending the extract in n-hexane and then decanting the waxes by severe cooling.

As disclosed herein, cannabis extracts with a high concentration of $\Delta^9$-tetrahydrocannabinol acid (THCA) and $\Delta^9$-tetrahydrocannabinol (THC) can be obtained by supercritical $CO_2$ extraction. By finetuning extraction pressure and temperature, the $CO_2$ solvent strength can be tuned, which provides selectivity to the extraction process. Regardless of the rising popularity and usage of supercritical $CO_2$ extraction, there is very limited reported information about the efficiency of the extraction process for cannabis plant material, much less the favorable extraction conditions and cannabinoids concentration on the extracts.

The use of co-solvent, such as propane, propene, and/or propadiene in the present disclosure, can improve the separation. However, the choice of co-solvents depends on the system. Although these co-solvents cannot be as flexibly manipulated through temperature and pressure as $CO_2$, they produce very similar results, sometimes better. For example, propane has a small loading ratio of 1-4 volumes, and it can be recovered quickly. This means much faster production times. Also, it is an all-natural, organic solvent and leaves no toxic residues. Importantly, because it works at relatively low pressures, e.g., 80-150 psi, the methods as disclosed herein cost much less than a full supercritical $CO_2$ system and are superior in terms of quality and speed of production. Accordingly, the present invention offers advantages over conventional extraction methods, including increased selectivity, automaticity, environmental safety, superior quality of extracts, and drastically decreased solvent residue.

As used herein, "extract" refers to a substance obtained by extracting a raw material, using, for example, the disclosed supercritical solvent system. The term "cannabis extract" refers to a substance obtained by extracting *Cannabis* (or any part thereof). For example, the process of extracting a raw cannabis material using a solvent includes a hot solvent extraction. In another example, the process of extracting a raw material using a solvent includes supercritical fluid extraction (SFE), e.g., a fractional supercritical fluid extraction (FSFE).

In some embodiments, the cannabis extract comprises terpene oil. In some embodiments, the extraction efficiency of terpene is at least 50% higher than a predetermined reference value. As used herein, "terpene" refers to a hydrocarbon or derivative thereof, found as a natural product and biosynthesized by oligomerization of isoprene units. A terpene can be acyclic, monocyclic, bicyclic, or multicyclic. Examples include limonene, pulegone, caryophyllene epoxide, and the like.

Terpenes are organic hydrocarbons that occur naturally in the essential oils of plants. Technically, terpenes are a combination of carbon and hydrogen. Though the names are used interchangeably, terpenoids are terpenes that have been altered through a drying process. Terpenes are responsible for the smell of cannabis, not only have their own individual medicinal properties, but they also work in conjunction with each other and the other cannabinoids to create the overall effect of a strain.

Terpenes are responsible for the scent and flavor of individual cannabis strains. The to concentration of terpenes can provide as many benefits as potency and cannabinoid content. From anti-inflammatory to chronic pain relief, the world of cannabis terpenes offers an impressive variety of therapeutic properties. These compounds define the flavor and aroma of our favorite plant but can also alter the high from cannabis.

Terpenes can intensify or downplay the effects of the cannabinoids. Carbonization destroys many of the terpenes, just like it destroys many of the cannabinoids. Like cannabinoids, terpenes have their own individual optimal temperature, and these temperatures can vary widely. As the demand for terpene-rich products has increased, a variety of product lines have come out, featuring cannabis concentrates infused with isolated terpenes.

In some embodiments, the cannabis extract comprises one or more cannabinoids selected from the group consisting of: tetrahydrocannabinol (THC), cannabidiol (CBD), cannabinol (CBN), cannabigerol (CBG), cannabichromene (CBC), cannabicyclol (CBL), cannabivarin (CBV), tetrahydrocannabivarin (THCV), cannabidivarin (CBDV), cannabichromevarin (CBCV), cannabigerovarin (CBGV), cannabigerol monomethyl ether (CBGM), and a combination thereof.

In some embodiments, the cannabis plant material is processed from *Cannabis sativa* or *Cannabis indica*. The cannabis plant material may or may not need to be pre-processed. For example, the raw cannabis plant material can be used directly for cannabis extraction. In some embodiments, the method further comprises grinding *Cannabis sativa* or *Cannabis indica* into ground cannabis plant material.

As used herein, "*Cannabis sativa* L." or "*Cannabis sativa*" refers to an annual herbaceous plant in the *Cannabis* genus, a species of the Cannabaceae family. As used herein, "*Cannabis indica* Lam" or "*Cannabis indica*" refers to an annual plant in the Cannabaceae family. A putative species of the genus *Cannabis*, it is typically distinguished from *Cannabis sativa*. *Cannabis sativa* and *Cannabis indica* can interbreed, so the two strains can be viewed as sub-species or landraces. Interbred stains comprising genetic material from both sativa and indica strains can be termed "sativa-dominant" or "indica-dominant," depending upon perceived physical and psychotropic properties of the hybrids. The mixed interbred strains can be themselves reproductively viable.

As used herein, "*Cannabis ruderalis* Janisch" or "*Cannabis ruderalis*" refers to a species of *Cannabis* originating in central Russia. It flowers earlier than *C. indica* or *C. sativa*, does not grow as tall, and can withstand much harsher climates than either of them. *Cannabis ruderalis* will produce flowers based on its age, rather than light cycle (photoperiod) changes which govern flowering in *C. sativa* and *C. indica* varieties. This kind of flowering is also known as "auto flowering."

As used herein, "*Cannabis*" refers to a genus of flowering plants that includes a single species, *Cannabis sativa*, which is sometimes divided into two additional species, *Cannabis indica* and *Cannabis ruderalis*. These three taxa are indigenous to Central Asia, and South Asia. *Cannabis* has long been used for fiber (hemp), for seed and seed oils, for medicinal purposes, and as a recreational drug. Various extracts including hashish and hash oil are also produced from the plant. Suitable strains of *Cannabis* include, e.g., Indica-dominant (e.g., Blueberry, BC Bud, Holland's Hope, Kush, Northern Lights, Purple, and White Widow), Pure sativa (e.g., Acapulco Gold and Malawi Gold (Chamba)), and Sativa-dominant (e.g., Charlotte's Web, Diesel, Haze, Jack Herer, Shaman, Skunk, Sour, and Te Puke Thunder). *Cannabis* plant material can include any physical part of the plant material, including, e.g., the leaf, bud, flower, trichome, seed, or combination thereof. Likewise, the cannabis plant material can include any substance physically derived from cannabis plant material, e.g., kief and hashish.

As used herein, "kief" refers to the resin glands (or trichomes) of *Cannabis*, which may accumulate in containers or be sifted from loose dry cannabis flower with a mesh screen or sieve. Kief typically contains a much higher concentration of psychoactive cannabinoids, such as THC, than that of the cannabis flowers from which it is derived. Traditionally, kief has been pressed into cakes of hashish for convenience in storage, but can be vaporized or smoked in either form.

As used herein, "hashish" refers to a cannabis product composed of compressed or purified preparations of stalked resin glands, called trichomes. It contains the same active ingredients—such as THC and other cannabinoids—but in higher concentrations than unsifted buds or leaves.

As used herein, "leaf" refers to an organ of a vascular plant, as defined in botanical terms, and in particular, in plant morphology. In reference to cannabis, the first pair of leaves usually have a single leaflet, the number gradually increasing up to a maximum of about thirteen leaflets per leaf (usually seven or nine), depending on variety and growing conditions. At the top of a flowering plant, this number again diminishes to a single leaflet per leaf. The lower leaf pairs usually occur in an opposite leaf arrangement and the upper leaf pairs in an alternate arrangement on the main stem of a mature plant.

As used herein, "bud" refers to a flower-bearing stem or branch of the cannabis plant, especially a stem or branch bearing a mass of female flowers with associated leaves. The stem or branch bearing the female flowers can be fresh or can be dried. The pistils of the female cannabis flower are surrounded by a mass of trichome-rich petals and leaves and can contain higher concentrations of cannabinoids than do the plant leaves or stems. A bud, e.g., a mass of female flowers and associated leaves, usually covered with trichomes, can be further processed mechanically, i.e., "trimming" or "cleaning" the stem bearing the female flowers by removal of larger leaves and stem material. Buds, and cleaned buds, can be used as a cannabis plant material in practice of a method of the invention.

As used herein, "trichome" refers to a fine outgrowth or appendage on plants and certain protists. They are of diverse structure and function. Examples are hairs, glandular hairs, scales, and papillae. In reference to cannabis, the trichome is a glandular trichome that occurs most abundantly on the floral calyxes and bracts of female plants.

As used herein, "seed" refers to an embryonic plant enclosed in a protective outer covering called the seed coat, usually with some stored food. It is a characteristic of spermatophytes (gymnosperm and angiosperm plants) and the product of the ripened ovule, which occurs after fertilization and some growth within the mother plant. The formation of the seed completes the process of reproduction in seed plants (started with the development of flowers and pollination), with the embryo developed from the zygote and the seed coat from the integuments of the ovule.

One of the advantages of the disclosed methods is that they result in significantly reduced wax formation during the extraction process. Thus, the degumming and dewaxing process in the conventional extraction methods can be eliminated. As a result, the present invention reduces energy consumption and production cost/time. In some embodiments, the wax formation during the extraction process is reduced by at least 10% compared to a predetermined reference value.

In some embodiments, the method further comprises purifying the cannabis extract by employing at least one of chromatography, adsorption, crystallization, distillation, liquid-liquid extraction, filtration, fractional distillation, precipitation, recrystallization, and sublimation.

As used herein, "purifying" refers to a process of rendering a substance, or a set of substances, pure, i.e., substantially free of, or having a lower relative content of, undesirable components. For example, the purified substance can be at least about 90% pure, at least about 95% pure, or at least about 98% pure.

B. Systems for Cannabis Extraction

In another aspect, this disclosure also provides a $CO_2$/hydrocarbon extraction system, as represented schematically in FIG. 1.

As depicted in TABLE 1. depending on trim potency, which varies from 8% to 12%, the cannabinoids potency results and efficiency will increase. The range and detailed experimental results can be observed as follows:

TABLE 1

Experiment Results for Trim Potency from
8% to 12% for $CO_2$ Only Extraction
$CO_2$ Extraction

| Trim Potency (%) | Cannabinoids Potency Results (%) | Efficiency (%) |
|---|---|---|
| 8 | 53 | 54 |
| 8 | 54 | 56 |
| 8 | 56 | 58 |
| 8 | 52 | 52 |
| 8 | 54 | 56 |
| 8 | 57 | 59 |
| 8 | 55 | 57 |
| 8 | 53 | 55 |
| 9 | 53 | 57 |
| 9 | 55 | 58 |
| 9 | 54 | 58 |
| 9 | 56 | 59 |
| 9 | 55 | 58 |
| 9 | 57 | 59 |
| 9 | 54 | 58 |
| 9 | 57 | 59 |
| 10 | 55 | 59 |
| 10 | 56 | 61 |
| 10 | 58 | 62 |
| 10 | 55 | 59 |
| 10 | 56 | 59 |
| 10 | 56 | 59 |
| 10 | 58 | 62 |
| 10 | 57 | 61 |
| 11 | 56 | 60 |
| 11 | 61 | 63 |
| 11 | 60 | 62 |
| 11 | 58 | 61 |
| 11 | 59 | 61 |
| 11 | 57 | 60 |
| 11 | 61 | 63 |
| 11 | 60 | 62 |
| 12 | 64 | 66 |
| 12 | 63 | 65 |
| 12 | 61 | 63 |
| 12 | 62 | 64 |
| 12 | 63 | 65 |
| 12 | 63 | 65 |
| 12 | 64 | 66 |
| 12 | 62 | 64 |

In some embodiments, the extraction system may include at least one extractor and at least one heating system (heater). In some embodiments, the extraction system may include, for example, 1 to 30 extractors in parallel. Each extractor may have various capacities, e.g., 20 L, as supported by two $CO_2$/hydrocarbon pumping systems (one for gas and one for liquid).

The heating system heats up the extracted oil up to 115° F. and the depressurized liquid mixture from the top of the extractor to about 180-480 psi (depending on the hydrocarbon and its fraction in blend) and gasifies the blend. In some embodiments, the extraction system may include at least one condensing system to cool down and liquefy the gas blend at 650-800 psi so as to keep the trim vessel cold to ensure that no waxes are being produced in the final product and two extract collection vessels, such as cannabinoid oil vessel and terpene vessel. All equipment are sized and configured to satisfy the output of the extractor(s).

The trim is fed to the extractor vessel initially. The next step is to feed $CO_2$ and hydrocarbon from the respective reservoirs (e.g., CO2 reservoir, hydrocarbon reservoir) to the accumulator in proper mole fractions. Both the accumulator and extractor vessels are kept at low temperatures (32-38° F.) to ensure there will be no waxes in the final product. The accumulator pressure is above 650-800 psi, with the $CO_2$/hydrocarbon existing as liquid therein.

The gas mixture is recycled with a loop, as shown in FIG. 1. The liquid blend will then be depressurized to proper pressure, e.g., by valve 3 in FIG. 1, and the heater will provide proper temperature to get into the gas phase. The gas blend then cooled down and fed to the extractor in a loop.

The trim vessel pressure is kept at 1050-1200 psi and 32-38° F. to keep the extraction efficiency high. Another novel feature of this extraction system is the capability of controlling the temperature inside the extractor. The gas blend stays in the gas phase under specific pressure and temperature. By expanding the blend at lower pressure, the temperature inside the extractor will drop, which helps to control the amount of waxes in the final product without requiring any external cooling system. The cold temperature inside the extractor ensures no waxes are being separated and produced in the final product vessel.

Adding hydrocarbons, such as propane and propene, as co-solvents to $CO_2$ will strongly increase potency results from 52-64% to 75-92%. The extraction efficiency will also increase from 56-66% to 79-95%. Terpenes extraction yield is also increased by up to 90%. Adding 5-10% of propane/propene/propadiene will significantly decrease energy consumption for the compressor up to 45%. It should be mentioned that propene and propadiene act stronger compared to propane, and the potency results for propadiene is slightly higher than propane and propene The detailed experimental results for different trim potency and $CO_2$/Hydrocarbon extraction are given in Table 2.

TABLE 2

Experiment Results for Trim Potency from
8% to 12% for $CO_2$/Hydrocarbon Extraction
$CO_2$/Hydrocarbon

| Trim Potency (%) | Cannabinoids Potency Results (%) | Efficiency (%) |
|---|---|---|
| 8 | 76 | 77 |
| 8 | 77 | 78 |
| 8 | 75 | 76 |
| 8 | 79 | 80 |
| 8 | 83 | 84 |
| 8 | 81 | 82 |
| 8 | 80 | 81 |
| 8 | 82 | 83 |

TABLE 2-continued

Experiment Results for Trim Potency from
8% to 12% for CO$_2$/Hydrocarbon Extraction CO$_2$/Hydrocarbon

| Trim Potency (%) | Cannabinoids Potency Results (%) | Efficiency (%) |
|---|---|---|
| 9 | 78 | 82 |
| 9 | 84 | 87 |
| 9 | 85 | 88 |
| 9 | 86 | 89 |
| 9 | 83 | 86 |
| 9 | 83 | 86 |
| 9 | 82 | 85 |
| 9 | 85 | 88 |
| 10 | 82 | 87 |
| 10 | 79 | 85 |
| 10 | 86 | 90 |
| 10 | 88 | 92 |
| 10 | 88 | 92 |
| 10 | 86 | 90 |
| 10 | 87 | 91 |
| 10 | 85 | 89 |
| 11 | 84 | 87 |
| 11 | 90 | 93 |
| 11 | 89 | 92 |
| 11 | 88 | 91 |
| 11 | 89 | 92 |
| 11 | 90 | 93 |
| 11 | 87 | 90 |
| 11 | 86 | 89 |
| 12 | 88 | 88 |
| 12 | 92 | 95 |
| 12 | 91 | 91 |
| 12 | 90 | 90 |
| 12 | 92 | 95 |
| 12 | 90 | 90 |
| 12 | 87 | 87 |
| 12 | 86 | 86 |

The current temperature for the trim vessel is 95-115° F., which will result in wax formation in the final oil. Reducing the temperature in the trim vessel to 32° F. (or even lower) will minimize the wax formation in the final product. Therefore, there is no need for a dewaxing/degumming process, which will result in more expenses savings.

In another aspect, this disclosure also provides a system for cannabis extraction. The system comprises (a) at least one extractor configured to receive plant material and a supercritical fluid solvent system comprising CO$_2$ and a hydrocarbon co-solvent; (b) an accumulator connected to the extractor and configured to feed the supercritical fluid solvent system to the extractor; and (c) at least one container connected to the extractor and configured to receive the extract generated from the plant material.

In some embodiments, the plant material is cannabis plant material. In some embodiments, the plant material is processed from *Cannabis sativa* or *Cannabis indica*.

In some embodiments, the system further comprises a first reservoir for CO$_2$ and a second reservoir for the hydrocarbon co-solvent, wherein the first reservoir and the second reservoir are connected to the accumulator and configured to feed CO$_2$ and the hydrocarbon co-solvent to the accumulator in which CO$_2$ and the hydrocarbon co-solvent are blended at a predetermined molar ratio.

In some embodiments, the system further comprises a heater connected with both the accumulator and the extractor, wherein the heater heats the supercritical fluid solvent system after the supercritical fluid solvent system passes through the plant material in the extractor, whereby the heated supercritical fluid solvent system is fed back to the accumulator.

In some embodiments, the hydrocarbon co-solvent is selected from the group consisting of propane, propene, propadiene, and a combination thereof. In some embodiments, the predetermined molar ratio of carbon dioxide to the hydrocarbon co-solvent is between about 0.75 to about 0.25 and about 0.99 to about 0.01 (e.g., 0.8:0.2; 0.85:0.15; 0.9:0.1; 0.92:0.08; 0.94:0.06; 0.95:0.05; 0.96:0.04; 0.98:0.02). In some embodiments, the predetermined molar ratio of carbon dioxide to the hydrocarbon co-solvent is about 0.95 to about 0.05.

In some embodiments, the accumulator is configured to provide the supercritical fluid solvent system with a pressure between about 650 psi and about 800 psi. In some embodiments, the accumulator is configured to provide the supercritical fluid solvent system with a temperature between about 32° F. and about 38° F.

In some embodiments, the extract comprises terpene oil. In some embodiments, the extract comprises one or more cannabinoids selected from the group consisting of: tetrahydrocannabinol (THC), cannabidiol (CBD), cannabinol (CBN), cannabigerol (CBG), cannabichromene (CBC), cannabicyclol (CBL), cannabivarin (CBV), tetrahydrocannabivarin (THCV), cannabidivarin (CBDV), cannabichromevarin (CBCV), cannabigerovarin (CBGV), cannabigerol monomethyl ether (CBGM), and a combination thereof.

In some embodiments, the wax formation is reduced by at least 10% compared to a predetermined reference value.

The disclosed systems and methods are also amenable for producing infused coffee/tea. In some embodiments, the plant material is coffee or tea leaves. The coffee/tea leaves can be fed to the extractor(s) with trim at the same operating conditions (temperature and pressures), as mentioned above. The cold temperature ensures high-quality coffee/tea production.

C. Compositions for Cannabis Extracts

In another aspect of this disclosure, also provided is a composition comprising the cannabis extract prepared by the method and system as described above. The composition further comprises an additive, a pharmaceutical acceptable carrier, or an adjuvant to the cannabis component.

The composition can be an oral dosage composition, a pulmonary or nasal dosage composition, or a topical dosage composition. The compositions can be in the form of a solution, a spray, or a powder. In some embodiments, the composition is in the form of a tablet, a capsule, a jelly, a cream, an ointment, a suspension, a spray, or a chewing gum.

In certain embodiments, the compositions as described herein are administered via a vaporizer or like device as described, for example, in U.S. Pat. No. 8,915,254; U.S. Pat. Appl. Pub. No. 2014/0060552; U.S. Pat. No. 8,488,952; and U.S. Pat. Appl. Pub. No. 2015/0040926. Compositions for pulmonary administration also include, but are not limited to, dry powder compositions consisting of the powder of a cannabis oil described herein, and the powder of a suitable carrier and/or lubricant. The compositions for pulmonary administration can be inhaled from any suitable dry powder inhaler device known to a person skilled in the art. In certain instances, the compositions may be conveniently delivered in the form of an aerosol spray from pressurized packs or a nebulizer, with the use of a suitable propellant, for example, dichlorodifluoromethane, trichlorofluoromethane, dichlorotetrafluoroethane, carbon dioxide, or other suitable gas. In the case of a pressurized aerosol, the dosage unit can be determined by providing a valve to deliver a metered amount. Capsules and cartridges of, for example, gelatin for use in an inhaler or insufflator can be formulated containing a powder mix of the compound(s) and a suitable powder base, for example, lactose or starch.

Pharmaceutical compositions or medicaments can be formulated by standard techniques or methods well-known in the art of pharmacy using one or more physiologically acceptable carriers or excipients. Suitable pharmaceutical carriers are described herein and in, e.g., "Remington's Pharmaceutical Sciences" by E. W. Martin. Cannabis oil extracts can be formulated for administration by any suitable route, including, but not limited to, orally, topically, nasally, rectally, vaginally, pulmonary, parenterally (e.g., intravenously, subcutaneously, intramuscularly, etc.), and combinations thereof. In some embodiments, the cannabis oil is diluted in a liquid, e.g., a carrier oil. The most suitable route of administration in any given case will depend in part on the condition being treated as well as the response of the subject to the particular route of treatment.

For oral administration, a pharmaceutical composition or a medicament can take the form of, e.g., a tablet or a capsule prepared by conventional means with a pharmaceutically acceptable excipient. Preferred are tablets and gelatin capsules comprising the active ingredient(s), together with (a) diluents or fillers, e.g., lactose, dextrose, sucrose, mannitol, maltodextrin, lecithin, agarose, xanthan gum, guar gum, sorbitol, cellulose (e.g., ethyl cellulose, microcrystalline cellulose), glycine, pectin, polyacrylates and/or calcium hydrogen phosphate, calcium sulfate, (b) lubricants; e.g., silica, anhydrous colloidal silica, talcum, stearic acid, its magnesium or calcium salt (e.g., magnesium stearate or calcium stearate), metallic stearates, colloidal silicon dioxide, hydrogenated vegetable oil, corn starch, sodium benzoate, sodium acetate and/or polyethyleneglycol; for tablets also (c) binders, e.g., magnesium aluminum silicate, starch paste, gelatin, tragacanth, methylcellulose, sodium carboxymethylcellulose, polyvinylpyrrolidone and/or hydroxypropyl methylcellulose; if desired (d) disintegrants, e.g., starches (e.g., potato starch or sodium starch), glycolate, agar, alginic acid or its sodium or potassium salt, or effervescent mixtures; (e) wetting agents, e.g., sodium lauryl sulfate, and/or (f) absorbents, colorants, flavors, and sweeteners. Tablets can be either uncoated or coated according to methods known in the art. The excipients described herein can also be used for preparation of buccal dosage forms and sublingual dosage forms (e.g., films and lozenges) as described, for example, in U.S. Pat. Nos. 5,981,552 and 8,475,832. Formulation in chewing gums as described, for example, in U.S. Pat. No. 8,722,022, is also contemplated.

Further preparations for oral administration can take the form of, for example, solutions, syrups, suspensions, and toothpastes. Liquid preparations for oral administration can be prepared by conventional means with pharmaceutically acceptable additives, for example, suspending agents, for example, sorbitol syrup, cellulose derivatives, or hydrogenated edible fats; emulsifying agents, for example, lecithin, xanthan gum, or acacia; non-aqueous vehicles, for example, almond oil, sesame oil, hemp seed oil, fish oil, oily esters, ethyl alcohol, or fractionated vegetable oils; and preservatives, for example, methyl or propyl-p-hydroxybenzoate or sorbic acid. The preparations can also contain buffer salts, flavoring, coloring, and/or sweetening agents as appropriate.

Typical formulations for topical administration include creams, ointments, sprays, lotions, hydrocolloid dressings, and patches, as well as eye drops, ear drops, and deodorants. Cannabis oils can be administered via transdermal patches as described, for example, in U.S. Pat. Appl. Pub. No. 2015/0126595 and U.S. Pat. No. 8,449,908. Formulation for rectal or vaginal administration is also contemplated. The cannabis oils can be formulated, for example, using suppositories containing conventional suppository bases such as cocoa butter and other glycerides as described in U.S. Pat. Nos. 5,508,037 and 4,933,363. Compositions can contain other solidifying agents such as shea butter, beeswax, kokum butter, mango butter, illipe butter, tamanu butter, carnauba wax, emulsifying wax, soy wax, castor wax, rice bran wax, and candelilla wax. Compositions can further include clays (e.g., Bentonite, French green clays, Fuller's earth, Rhassoul clay, white kaolin clay) and salts (e.g., sea salt, Himalayan pink salt, and magnesium salts such as Epsom salt).

The compositions set forth herein can be formulated for parenteral administration by injection, for example, by bolus injection or continuous infusion. Formulations for injection can to be presented in unit dosage form, for example, in ampoules or in multi-dose containers, optionally with an added preservative. Injectable compositions are preferably aqueous isotonic solutions or suspensions, and suppositories are preferably prepared from fatty emulsions or suspensions. The compositions may be sterilized and/or contain adjuvants, such as preserving, stabilizing, wetting or emulsifying agents, solution promoters, salts for regulating the osmotic pressure, buffers, and/or other ingredients. Alternatively, the compositions can be in powder form for reconstitution with a suitable vehicle, for example, a carrier oil, before use. In addition, the compositions may also contain other therapeutic agents or substances.

The compositions can be prepared according to conventional mixing, granulating, and/or coating methods and contain from about 0.1 to about 75%, preferably from about 1 to about 50%, of the cannabis oil extract. In general, subjects receiving a cannabis oil composition orally are administered doses ranging from about 1 to about 2000 mg of cannabis oil. A small dose ranging from about 1 to about 20 mg can typically be administered orally when treatment is initiated, and the dose can be increased (e.g., doubled) over a period of days or weeks until the maximum dose is reached.

In some embodiments, the composition is an oral dosage composition, a pulmonary or nasal dosage composition, or a topical dosage composition. The composition may be in the form of a solution, a spray, or a powder, a tablet, a capsule, a jelly, a cream, an ointment, a suspension, a spray, or a chewing gum.

Also within the scope of this disclosure is a unit dose of the composition as described above. In some embodiments, the unit dose comprises an amount of the composition selected from the group consisting of: trace amount, 0.01-0.05 mg, 0.05-0.1 mg, 0.1-0.5 mg, 0.25-1 mg, 0.5-15 mg, 0.5-2.5 mg, 1.0-2.5 mg, 2.5-5 mg, 5.0-7.5 mg, 5.0-10 mg, 1.0-25 mg, 25-50 mg, 50-75 mg, 75-100 mg, 10-20 mg, 10-15 mg, and 15-20 mg, 20-30 mg, 30-40 mg, 40-50 mg, 50-60 mg, 60-70 mg, 70-80 mg, 80-90 mg, 90-100 mg, 1-100 mg, 100-125 mg, 125-150 mg, 150-175 mg, 175-200 mg, and >200 mg.

In some embodiments, the composition may further comprise a second agent selected from the group consisting of: cannabinoids, terpenes, anti-insomnia, anti-tussive, opioid analgesic, decongestant, non-opioid analgesic/anti-inflammatory drug, anti-migraine drug, anti-emetic, anti-histamine, proton pump inhibitor, H2 antagonist/H2 blocker, tranquilizer, anticonvulsant, hypnotic, muscle relaxant, antipsychotic, anti-diarrheal, Attention Deficit and Hyperactivity Disorder (ADHD) drug, anti-Parkinson disease drug, benzodiazepine, benzodiazepine antagonist, barbiturate, barbiturate antagonist, stimulant, stimulant antagonist, antidepressant, nutraceutical, nicotine, BCS Class II active ingredient, BCS Class IV active ingredient, an anti-multiple sclerosis (MS) drug, ethyl pyruvate, melatonin, caffeine, resveratrol, and a combination thereof.

In some embodiments, the second agent is selected from the group consisting of: CBD, THC, CBN, CBG, CBC, THCA, CBDA, THCV, and a combination thereof.

In some embodiments, the composition at therapeutically effective concentrations or dosages be combined with a pharmaceutically or pharmacologically acceptable carrier, excipient or diluent, either biodegradable or non-biodegradable.

For example, the composition may be administered in the pure form or in a pharmaceutically acceptable formulation including suitable elixirs, binders, and the like (also generally referred to a "carriers") or as pharmaceutically acceptable salts (e.g., alkali metal salts such as sodium, potassium, calcium or lithium salts, ammonium, etc.) or other complexes. It should be understood that the pharmaceutically acceptable formulations include liquid and solid materials conventionally utilized to prepare both injectable dosage forms and solid dosage forms such as tablets and capsules and aerosolized dosage forms. In addition, the compounds may be formulated with aqueous or oil-based vehicles. Water may be used as the carrier for the preparation of compositions (e.g., injectable compositions), which may also include conventional buffers and agents to render the composition isotonic. Other potential additives and other materials (preferably those which are generally regarded as safe [GRAS]) include: colorants; flavorings; surfactants (TWEEN, oleic acid, etc.); solvents, stabilizers, elixirs, and binders or encapsulants (lactose, liposomes, etc). Solid diluents and excipients include lactose, starch, conventional disintegrating agents, coatings and the like. Preservatives such as methylparaben or benzalkonium chloride may also be used. Depending on the formulation, it is expected that the active composition will consist of about 1% to about 99% of the composition and the vehicular "carrier" will constitute about 1% to about 99% of the composition. The pharmaceutical compositions of the present invention may include any suitable pharmaceutically acceptable additives or adjuncts to the extent that they do not hinder or interfere with the therapeutic effect of the active compound.

Examples of carriers include, but are by no means limited to, for example, poly(ethylene-vinyl acetate), copolymers of lactic acid and glycolic acid, poly(lactic acid), gelatin, collagen matrices, polysaccharides, poly(D,L lactide), poly (malic acid), poly(caprolactone), celluloses, albumin, starch, casein, dextran, polyesters, ethanol, methacrylate, polyurethane, polyethylene, vinyl polymers, glycols, mixtures thereof and the like. Standard excipients include gelatin, casein, lecithin, gum acacia, cholesterol, tragacanth, stearic acid, benzalkonium chloride, calcium stearate, glyceryl monostearate, cetostearyl alcohol, cetomacrogol emulsifying wax, sorbitan esters, polyoxyethylene alkyl ethers, polyoxyethylene castor oil derivatives, polyoxyethylene sorbitan fatty acid esters, polyethylene glycols, polyoxyethylene stearates, colloidal silicon dioxide, phosphates, sodium dodecyl sulfate, carboxymethylcellulose calcium, carboxymethylcellulose sodium, methylcellulose, hydroxyethylcellulose, hydroxypropyl cellulose, hydroxypropyl-methylcellulose phthalate, noncrystalline cellulose, magnesium aluminum silicate, triethanolamine, polyvinyl alcohol, polyvinylpyrrolidone, sugars, and starches. See, for example, Remington: The Science and Practice of Pharmacy, 1995, Gennaro ed.

In some embodiments, the chemicals can be purified and blended together to produce a formulation similar in form to that for Marinol®. In these formulations, the active ingredient is dissolved in sesame seed oil or similar oil and enclosed in a gel-capsule. In other embodiments, the formulation may be arranged to be used as an injectable or as an aerosol. In these embodiments, as will be apparent to one of skill in the art, the appropriate pharmaceutically-acceptable additives may be added so that the pharmaceutical composition is in the appropriate form.

As will be appreciated by one knowledgeable in the art, the formulation may be used as, for example, an anti-emetic, appetite stimulant, or as a treatment for nausea, dementia, Alzheimer's disease, glaucoma, high blood pressure, inflammation or multiple sclerosis. For example, when administered to an individual in need of such treatment, the pharmaceutical composition of $\Delta^8$-THC and CBD will accomplish at least one of the following: reduce nausea, promote or stimulate appetite, reduce vomiting and/or promote a general feeling of well-being.

Additional Ingredients

Cannabinoids are susceptible to oxidation and hydrolysis. Over time it is possible for cannabinoids to be exposed to oxygen, hydrogen ions (acids, water), in addition to any other environmental factors that will cause their degradation.

Organic bases can be used to prevent the degradation of the cannabinoids. These organic bases include, but are not limited to, butyl hydroxyl anisole (BHA), butyl hydroxyl toluene (BHT), and sodium ascorbate; at concentrations between 0.001 to 5%> w/w, for example. Organic bases such as the following can improve the stability of cannabinoids from chemical degradation for up to 2 years: BHA 0.001 to 5% w/w, BHT 0.001 to 5% w/w, and combinations of BHA and BHT can also be used.

Antioxidants can be used to prevent or at least inhibit or mitigate the degradation of cannabinoids from oxidation. Examples of antioxidants include: ethanol, polyethylene glycol 300, polyethylene glycol 400, propylene glycol, propylene carbonate, N-methyl-2-pyrrolidones, dimethylacetamide, dimethyl sulfoxide, hydroxypropyl-P-cyclodextrins, sulfobutylether-β-cyclodextrin, a-cyclodextrin, HSPC phospholipid, DSPG phospholipid, DMPC phospholipid, DMPG phospholipid, ascorbyl palmitate, butylated hydroxyanisole, butylated hydroxyanisole, propyl gallate, a-tocopherol, γ-tocopherol, propyl gallate, lecithin, Vitamin E tocopherol, sesamin, sesamol, sesamolin, alpha-tocopherol, ascorbic acid, ascorbyl palmitate, fumaric acid, malic acid, sodium metabisulfite, and EDTA. Specific antioxidant examples include, but are not limited to: Ascorbic Acid: 0.001 to 5% w/w, Vitamin E Tocopherol: 0.001 to 5% w/w, Tocopherol: 0.001 to 5% w/w, and combinations of ascorbic acid, vitamin E tocopherol, and tocopherol can be used for this invention.

Chelating agents can prevent or at least mitigate the degradation of cannabinoids from metal ions in solution. Chelating agents include, but are not limited to, ethylenediaminetetraacetic acid (EDTA), phosphoric acid, polyphosphates, polysaccharides, citric acid, and any combination thereof.

Preservatives can be used to prevent microbial spoilage. These preservatives include: methylparabens, ethylparabens, propylparabens, butylparabens, sorbic acid, acetic acid, propionic acid, sulfites, nitrites, sodium sorbate, potassium sorbate, calcium sorbate, benzoic acid, sodium benzoate, potassium benzoate, calcium benzoate, sodium metabisulfite, propylene glycol, benzaldehyde, butylated hydroxytoluene, butylated hydroxyanisole, formaldehyde donors, essential oils, citric acid, monoglyceride, phenol, mercury components and any combination thereof. Specific examples include, but are not limited to, sodium benzoate and potassium sorbate.

Additionally, the pH can be lowered to prevent or retard microbial growth. Lowering the pH below 4.0 is sufficiently low enough to prevent microbial growth for a minimum of 1 month.

Preservatives and/or stabilizers can be added during formulation. Depending on the nature of the preservative/stabilizer, it may be contained in either the oil phase, interfacial layer, or the aqueous continuous phase. Once dissolved, the preservatives and stabilizers are released into solution imparting their properties into the aqueous system. This allows beverage manufacturers the ability to instantly create shelf-stable cannabis-infused beverages. Beverages made this way can resist microbial growth and chemical degradation for a minimum of 3 months.

The composition can be used for treatment of a subject afflicted with or suffering from nausea, muscular spasms, multiple sclerosis, uterine cramps, bowel cramps, a movement disorder, pain, migraine headache, vertigo, glaucoma, asthma, inflammation, insomnia, high blood pressure, cancer, anxiety, convulsions, depression or psychosis.

Accordingly, in another aspect, this disclosure provides a method of treatment of a subject. The method comprises administering to a subject afflicted with or suffering from nausea, muscular spasms, multiple sclerosis, uterine cramps, bowel cramps, a movement disorder, pain, migraine headache, vertigo, glaucoma, asthma, inflammation, insomnia, high blood pressure, cancer, anxiety, convulsions, depression or psychosis, an effective amount of the composition as described above.

In some embodiments, the composition is administered intratumorally, intravenously, subcutaneously, intraosseously, orally, transdermally, in sustained release, in controlled release, in delayed release, as a suppository, or sublingually. In some embodiments, the composition is administered once, twice, three, or four times per day, or as needed.

The administration of the composition invention may be intermittent, bolus dose, or at a gradual or continuous, constant or controlled rate to a patient. In addition, the time of day and the number of times per day that the pharmaceutical formulation is administered may vary and are best determined by a skilled practitioner such as a physician. Further, the effective dose can vary depending upon factors such as the mode of delivery, gender, age, and other conditions of the patient, as well as the extent or progression of the disease. The compounds may be provided alone, in a mixture containing two or more of the compounds, or in combination with other medications or treatment modalities. The compounds may also be added to blood ex vivo and then be provided to the patient.

In one aspect, this disclosure provides a kit comprising the composition as described above.

In some embodiments, the kit further comprising a beverage, wherein the composition and the beverage are in separate containers. In some embodiments, the kit may further include instructional materials.

"Instructional material," as that term is used herein, includes a publication, a recording, a diagram, or any other medium of expression that can be used to communicate the usefulness of any composition and/or compound of the invention in a kit. The instructional material of the kit may, for example, be affixed to a container that contains any composition of the invention or be shipped together with a container which contains any composition. Alternatively, the instructional material may be shipped separately from the container with the intention that the recipient uses the instructional material and any composition cooperatively. Delivery of the instructional material may be, for example, by physical delivery of the publication or other medium of expression communicating the usefulness of the kit, or may alternatively be achieved by electronic transmission, for example, by means of a computer, such as by electronic mail, or download from a website.

Also within the scope of this disclosure is an edible product comprising the composition as described above. In some embodiments, the edible product is selected from a lozenge, candy, chocolate, brownie, cookie, trail bar, cracker, dissolving strip, pastry, bread, or chewing gum.

TABLE 3

Experiment Results Summary
Method

| | CO2 Extraction | | | CO2/Hydrocarbon | |
| --- | --- | --- | --- | --- | --- |
| Trim Potency (%) | Cannabinoids Potency Results (%) | Efficiency (%) | Trim Potency (%) | Cannabinoids Potency Results (%) | Efficiency (%) |
| 8% | 52-57% | 56-59% | 8% | 75-83% | 79-84% |
| 9% | 53-57% | 57-60% | 9% | 77-86% | 81-89% |
| 10% | 55-59% | 59-62% | 10% | 79-88% | 83-92% |
| 11% | 56-62% | 60-64% | 11% | 83-90% | 87-93% |
| 12% | 62-64% | 63-66% | 12% | 86-92% | 90-95% |

D. Definitions

To aid in understanding the detailed description of the compositions and methods according to the disclosure, a few express definitions are provided to facilitate an unambiguous disclosure of the various aspects of the disclosure. Unless otherwise defined, all technical and scientific terms used herein have the same meaning as commonly understood by one of ordinary skill in the art to which this disclosure belongs.

The term "*cannabis*" refers to plants of the genus cannabis, including *Cannabis sativa, Cannabis indica,* and *Cannabis ruderalis.*

The term "cannabis oil" refers to a mixture of compounds obtained from the extraction of cannabis plants. Such compounds include, but are not limited to, cannabinoids, terpenes, terpenoids, and other compounds found in the cannabis plant. The exact composition of cannabis oil will depend on the strain of cannabis that is used for extraction, the efficiency and process of the extraction itself, and any additives that might be incorporated to alter the palatability or improve administration of the cannabis oil.

The term "cannabinoid" refers to a chemical compound that shows direct or indirect activity at a cannabinoid receptor. There are two main cannabinoid receptors, CNR1 (also known as CB1) and CNR2 (also known as CB2). Other receptors that research indicates have cannabinoid activity include the GPR55, GPR18, and TRPV1 receptors. The term "phytocannabinoid" refers to cannabinoids that occur in a plant species or are derived from cannabinoids occurring in a plant species. Examples of cannabinoids include, but are not limited to, tetrahydrocannabinol (THC), cannabidiol (CBD), cannabinol (CBN), cannabigerol (CBG), cannabichromene (CBC), cannabicyclol (CBL), cannabivarin (CBV), tetrahydrocannabivarin (THCV), cannabidivarin (CBDV), cannabichromevarin (CBCV), cannabigerovarin (CBGV), and cannabigerol monomethyl ether (CBGM).

As used herein, CBD refers to cannabidiol.

As used herein, $\Delta^9$-THC refers to $\Delta^9$-tetrahydrocannabinol.

As used herein, $\Delta^8$-THC refers to $\Delta^8$-tetrahydrocannabinol.

The term "acidic cannabinoid" refers to a cannabinoid having one or more carboxylic acid functional groups. Examples of acidic cannabinoids include, but are not limited to, tetrahydrocannabinolic acid (THCA), cannabidiolic acid (CBDA), and cannabichromenic acid (CBC). Acidic cannabinoids are frequently the predominant cannabinoids found in raw (i.e., unprocessed) cannabis plant material.

The term "essential oil" refers to natural plant oil typically obtained by distillation and having a chemical composition and organoleptic properties (e.g., fragrance) characteristic of the plant or other sources from which it is extracted.

As used herein, "anti-emetic" refers to compounds capable of reducing nausea, enhancing appetite and/or reducing vomiting in an individual.

By "water-soluble" we mean that 1 mg of material in 1 ml of water gives a clear solution and is water-miscible.

By "high affinity" we mean that the compounds exhibit a Ki in the range of about 0.03 nM to about 80 nM, and preferably from about 0.03 nM to about 50 nM, for either the CB1 or CB2 receptors, or both.

As used herein, "effective amount" refers to the administration of an amount of a given compound that achieves the desired effect. For example, regarding the combination of CBD and $\Delta^8$-THC, an "effective amount" is an amount sufficient for or that is capable of reducing nausea or vomiting and/or enhancing appetite in a patient or individual in need of such treatment. The patient may be a human patient.

As used herein, "purified" does not require absolute purity but is instead intended as a relative definition. For example, purification of starting material or natural material to at least one order of magnitude, preferably two or three orders of magnitude, is expressly contemplated as falling within the definition of "purified."

As used herein, the term "isolated" requires that the material be removed from its original environment.

As used herein, the terms "subject" and "patient" are used interchangeably irrespective of whether the subject has or is currently undergoing any form of treatment. As used herein, the terms "subject" and "subjects" may refer to any vertebrate, including, but not limited to, a mammal (e.g., cow, pig, camel, llama, horse, goat, rabbit, sheep, hamsters, guinea pig, cat, dog, rat, and mouse, a non-human primate (for example, a monkey, such as a cynomolgus monkey, chimpanzee, etc) and a human). The subject may be a human or a non-human. In this context, a "normal," "control," or "reference" subject, patient or population is/are one(s) that exhibit(s) no detectable disease or disorder, respectively.

"Sample," "test sample," and "patient sample" may be used interchangeably herein. The sample can be a sample of, serum, urine plasma, amniotic fluid, cerebrospinal fluid, cells (e.g., antibody-producing cells) or tissue. Such a sample can be used directly as obtained from a patient or can be pre-treated, such as by filtration, distillation, extraction, concentration, centrifugation, inactivation of interfering components, addition of reagents, and the like, to modify the character of the sample in some manner as discussed herein or otherwise as is known in the art. The terms "sample" and "biological sample" as used herein generally refer to a biological material being tested for and/or suspected of containing an analyte of interest such as antibodies. The sample may be any tissue sample from the subject. The sample may comprise protein from the subject.

The term "treating" or "treatment" refers to administration of a compound or agent to a subject who has a disorder or is at risk of developing the disorder with the purpose to cure, alleviate, relieve, remedy, delay the onset of, prevent, or ameliorate the disorder, the symptom of the disorder, the disease state secondary to the disorder, or the predisposition toward the disorder.

The terms "prevent," "preventing," "prevention," "prophylactic treatment" and the like refer to reducing the probability of developing a disorder or condition in a subject (e.g., plant), who does not have, but is at risk of or susceptible to developing a disorder or condition.

The terms "decrease," "reduced," "reduction," "decrease," or "inhibit" are all used herein generally to mean a decrease by a statistically significant amount. However, for the avoidance of doubt, "reduced," "reduction" or "decrease" or "inhibit" means a decrease by at least 10% as compared to a reference level, for example, a decrease by at least about 20%, or at least about 30%, or at least about 40%, or at least about 50%, or at least about 60%, or at least about 70%, or at least about 80%, or at least about 90% or up to and including a 100% decrease (e.g., absent level as compared to a reference sample), or any decrease between 10-100% as compared to a reference level.

It is noted here that, as used in this specification and the appended claims, the singular forms "a," "an," and "the" include plural reference unless the context clearly dictates otherwise.

The terms "including," "comprising," "containing," or "having" and variations thereof are meant to encompass the items listed thereafter and equivalents thereof as well as additional subject matter unless otherwise noted.

The phrases "in one embodiment," "in various embodiments," "in some embodiments," and the like are used repeatedly. Such phrases do not necessarily refer to the same embodiment, but they may unless the context dictates otherwise.

The terms "and/or" or "/" means any one of the items, any combination of the items, or all of the items with which this term is associated.

The word "substantially" does not exclude "completely," e.g., a composition which is "substantially free" from Y may be completely free from Y. Where necessary, the word "substantially" may be omitted from the definition of the invention.

As used herein, the term "approximately" or "about," as applied to one or more values of interest, refers to a value that is similar to a stated reference value. In some embodiments, the term "approximately" or "about" refers to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value). Unless indicated otherwise herein, the term "about" is intended to include values, e.g., weight percents, proximate to the recited range that are equivalent in terms of the functionality of the individual ingredient, the composition, or the embodiment.

As disclosed herein, a number of ranges of values are provided. It is understood that each intervening value, to the tenth of the unit of the lower limit, unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither, or both limits are included in the smaller ranges is also encompassed within the invention, subject to any specifically excluded limit in the stated range. Where the stated range includes one or both of the limits, ranges excluding either or both of those included limits are also included in the invention.

As used herein, the term "each," when used in reference to a collection of items, is intended to identify an individual item in the collection but does not necessarily refer to every item in the collection. Exceptions can occur if explicit disclosure or context clearly dictates otherwise.

The use of any and all examples or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

All methods described herein are performed in any suitable order unless otherwise indicated herein or otherwise clearly contradicted by context. In regard to any of the methods provided, the steps of the method may occur simultaneously or sequentially. When the steps of the method occur sequentially, the steps may occur in any order, unless noted otherwise. In cases in which a method comprises a combination of steps, each and every combination or sub-combination of the steps is encompassed within the scope of the disclosure, unless otherwise noted herein.

Each publication, patent application, patent, and other reference cited herein is incorporated by reference in its entirety to the extent that it is not inconsistent with the present disclosure. Publications disclosed herein are provided solely for their disclosure prior to the filing date of the present invention. Nothing herein is to be construed as an admission that the present invention is not entitled to antedate such publication by virtue of prior invention. Further, the dates of publication provided may be different from the actual publication dates, which may need to be independently confirmed.

It is understood that the examples and embodiments described herein are for illustrative purposes only and that various modifications or changes in light thereof will be suggested to persons skilled in the art and are to be included within the spirit and purview of this application and scope of the appended claims.

E. Examples

Example 1

Stepwise Time-Dependent Extraction of Terpenes and Cannabinoids

As a novel application for the disclosed $CO_2$/Hydrocarbon extraction system, fresh frozen material (about −5 to −10° C.) can be used to feed the reactor. The $CO_2$/Hydrocarbon system also further provides a cooler environment for the reactor, which will reduce the temperature inside the reactor to −30 to −50° C. (depends on the mixture ratio and gas accumulator pressure). In a timeframe of 5 to 30 minutes, high purity terpenes profiles can be extracted. After 30 minutes, high potency oil with lower terpene profiles can be extracted. Since fresh frozen is already cold with changing gas solvent accumulator (range from 200 psi to 550 psi), it will get lower temperatures in the reactor compared to the fresh one. Although the 400 to 450 psi is the optimum pressure range. Having a pressure of 400 to 450 psi in the gas accumulator will result in the temperature range of −40 to −50 C in the reactor. In one experiment, 72 grams of terpenes can be extracted in the first 30 minutes, and 355 grams of oil can be extracted in 20 hours, from about 7.0 kg fresh frozen at 10% and over 50 wt % water.

The disclosed methods and systems are advantageous compared to the fresh frozen hydrocarbon (70% Butane/30% Propane) extraction system, because a significantly lower amount of crystal THCa will be produced along with terpenes.

What is claimed is:

1. A method for cannabis extraction, comprising:
   (i) contacting cannabis plant material with a supercritical fluid solvent system comprising carbon dioxide ($CO_2$) and a hydrocarbon co-solvent at a temperature of from 30° C. to −50° C.;
   (ii) obtaining a first fraction of the supercritical fluid solvent system containing a high purity terpene first cannabis extract during a first period of time;
   (iii) obtaining a second fraction of the supercritical fluid solvent system containing a second cannabis extract during a second period of time; and
   (iv) removing the $CO_2$ and the hydrocarbon co-solvent from the first fraction of the supercritical fluid solvent system and the second fraction of the supercritical fluid solvent system, thereby obtaining the first cannabis extract and the second cannabis extract.

2. The method of claim 1, wherein the second cannabis extract comprises cannabinoids.

3. The method of claim 1, comprising freezing the cannabis plant material at a temperature of from about −5° C. to about −10° C.

4. The method of claim 1, wherein the first period of time is between about 2 minutes and about 30 minutes and the second period of time is between about 30 minutes and about 24 hours.

5. The method of claim 1, wherein the hydrocarbon co-solvent is selected from the group consisting of propane, propene, propadiene, and a combination thereof.

6. The method of claim 1, wherein a molar ratio of carbon dioxide to the hydrocarbon co-solvent is between about 0.75:0.25 and about 0.98:0.02.

7. The method of claim 1, wherein the step of contacting is performed at a pressure of between about 650 psi and about 800 psi.

8. The method of claim 1, comprising repeating steps (i) and (iv) at least once.

9. The method of claim 1, wherein the first cannabis extract comprises the high purity terpene as terpene oil.

10. The method of claim 1, wherein the second cannabis extract comprises one or more cannabinoids selected from the group consisting of:
   tetrahydrocannabinol (THC), cannabidiol (CBD), cannabinol (CBN), cannabigerol (CBG), cannabichromene (CBC), cannabicyclol (CBL), cannabivarin (CBV), tetrahydrocannabivarin (THCV), cannabidivarin (CBDV), cannabichromevarin (CBCV), cannabigerovarin (CBGV), and cannabigerol monomethyl ether (CBGM).

11. The method of claim 1, comprising processing the cannabis plant material from *Cannabis sativa* or *Cannabis indica*.

12. The method of claim 1, wherein the cannabis plant material comprises ground cannabis plant material.

13. The method of claim 1, further comprising purifying the cannabis extracts by employing at least one of chromatography, adsorption, crystallization, distillation, optionally comprising fractional distillation, liquid-liquid extraction, filtration, precipitation, recrystallization, and sublimation.

* * * * *